United States Patent
Hiblar et al.

(10) Patent No.: US 6,800,083 B2
(45) Date of Patent: Oct. 5, 2004

(54) COMPRESSIBLE ATHERECTOMY BURR

(75) Inventors: Thomas J. Hiblar, Everett, WA (US); Robert L. Barry, Kirkland, WA (US); Edward Wulfman, Woodinville, WA (US); Zihong Guo, Bellevue, WA (US); Verivada Chandru Chandrasekaran, Mercer Island, WA (US)

(73) Assignee: SciMed Life Systems, Inc., Maple Grove, MI (US)

( * ) Notice: Subject to any disclaimer, the term of this patent is extended or adjusted under 35 U.S.C. 154(b) by 399 days.

(21) Appl. No.: 09/829,486

(22) Filed: Apr. 9, 2001

(65) Prior Publication Data

US 2002/0147458 A1 Oct. 10, 2002

(51) Int. Cl.$^7$ ............................. A61B 17/32; A61D 1/02
(52) U.S. Cl. ...................... 606/159; 606/170; 606/171; 606/180; 604/22
(58) Field of Search ......................... 606/1, 108, 159, 606/170, 171, 180; 604/22; 15/304, 406, 165, 104.03, 104.05, 104.062

(56) References Cited

U.S. PATENT DOCUMENTS

| | | | |
|---|---|---|---|
| 2,701,559 A | 2/1955 | Cooper | |
| 3,614,953 A | 10/1971 | Moss | |
| 3,896,815 A | 7/1975 | Fettel et al. | |
| 4,273,128 A | 6/1981 | Lary | |
| 4,443,488 A | 4/1984 | Little et al. | |
| 4,465,072 A | 8/1984 | Taheri | |
| 4,530,125 A | * 7/1985 | Hofmann | 15/1.7 |
| 4,589,412 A | 5/1986 | Kensey | |
| 4,631,052 A | 12/1986 | Kensey | |
| 4,653,496 A | 3/1987 | Bundy et al. | |
| 4,685,458 A | 8/1987 | Leckrone | |
| 4,696,667 A | 9/1987 | Masch | |
| 4,728,319 A | 3/1988 | Masch | |
| 4,743,493 A | 5/1988 | Sioshansi et al. | |
| 4,747,821 A | 5/1988 | Kensey et al. | |
| 4,765,332 A | 8/1988 | Fischell et al. | |

(List continued on next page.)

FOREIGN PATENT DOCUMENTS

| | | |
|---|---|---|
| DE | 867144 | 4/1951 |
| EP | 0 086 048 | 8/1983 |

*Primary Examiner*—Henry Bennett
*Assistant Examiner*—Kathryn Odland
(74) *Attorney, Agent, or Firm*—Christensen O'Connor Johnson Kindness PLLC

(57) ABSTRACT

A rotational ablation atherectomy device including a flexible drive shaft and a compressible burr that may be inserted and extracted from a patient using a catheter having a diameter that is smaller than the operational diameter of the burr. In one embodiment, the burr includes a nose portion coupled to the drive shaft and one or more flexible abrasive disks disposed rearwardly from the nose portion. The flexible disks are foldable to be slidably received within a catheter. In another embodiment, the burr includes a support member coupled to the drive shaft, the support member having a resilient panel that spirals outwardly, forming a generally cylindrical ablation surface. The flexible panel can be elastically urged toward the support member and slidably inserted into the catheter. In a third embodiment, the burr includes a plurality of struts that are coupled to the drive shaft. An elastically compressible body disposed between the struts permits the struts to flex inwardly to reduce the burr diameter. In another embodiment, the burr includes a plurality of flexible wires attached at proximal and distal ends to the drive shaft. An abrasive sheath is disposed over the wires. The wires can be bent inwardly to compress the burr and re-expanded by rotation of the burr. In another embodiment, the burr comprises a nose portion and a resilient shell having a compressible, larger diameter abrasive section disposed at the proximal end of the nose portion.

12 Claims, 6 Drawing Sheets

U.S. PATENT DOCUMENTS

| | | | |
|---|---|---|---|
| 4,781,186 A | | 11/1988 | Simpson et al. |
| 4,784,636 A | | 11/1988 | Rydell |
| 4,794,928 A | | 1/1989 | Kletschka |
| 4,794,931 A | | 1/1989 | Yock |
| 4,842,579 A | | 6/1989 | Shiber |
| 4,850,957 A | * | 7/1989 | Summers ................. 604/22 |
| 4,857,045 A | | 8/1989 | Rydell |
| 4,886,061 A | | 12/1989 | Fischell et al. |
| 4,898,574 A | | 2/1990 | Uchiyama et al. |
| 4,926,858 A | | 5/1990 | Gifford, III et al. |
| 4,950,238 A | | 8/1990 | Sullivan |
| 4,966,604 A | | 10/1990 | Reiss |
| 4,990,134 A | | 2/1991 | Auth |
| RE33,569 E | | 4/1991 | Gifford, III et al. |
| 5,009,659 A | * | 4/1991 | Hamlin et al. ............ 606/159 |
| 5,030,201 A | | 7/1991 | Palestrant |
| 5,100,425 A | | 3/1992 | Fischell et al. |
| 5,192,291 A | | 3/1993 | Pannek, Jr. |
| 5,223,309 A | | 6/1993 | Farivar et al. |
| 5,224,945 A | | 7/1993 | Pannek, Jr. |
| 5,250,060 A | | 10/1993 | Carbo et al. |
| 5,318,576 A | | 6/1994 | Plassche, Jr. et al. |
| 5,376,100 A | | 12/1994 | Lefebvre |
| 5,385,311 A | | 1/1995 | Morikawa et al. |
| 5,395,311 A | | 3/1995 | Andrews |
| 5,411,509 A | * | 5/1995 | Hilal ........................ 606/159 |
| 5,457,841 A | * | 10/1995 | Minton ................. 15/104.061 |
| 5,468,562 A | | 11/1995 | Farivar et al. |
| 5,490,859 A | | 2/1996 | Mische et al. |
| 5,556,405 A | | 9/1996 | Lary |
| 5,569,276 A | | 10/1996 | Jang et al. |
| 5,571,086 A | | 11/1996 | Kaplan et al. |
| 5,649,941 A | | 7/1997 | Lary |
| 5,653,696 A | | 8/1997 | Shiber |
| 5,681,336 A | | 10/1997 | Clement et al. |
| 5,725,543 A | | 3/1998 | Redha |
| 5,725,568 A | | 3/1998 | Hastings |
| 5,749,914 A | | 5/1998 | Janssen |
| 5,766,192 A | | 6/1998 | Zacca |
| 5,842,479 A | | 12/1998 | Plaia et al. |
| 5,964,004 A | * | 10/1999 | Bean ..................... 15/104.16 |
| 6,015,420 A | | 1/2000 | Wulfman et al. |
| 6,096,054 A | | 8/2000 | Wyzgala et al. |
| 6,146,395 A | | 11/2000 | Kanz et al. |
| 6,183,487 B1 | | 2/2001 | Barry et al. |
| 6,270,509 B1 | | 8/2001 | Barry et al. |
| 6,299,623 B1 | | 10/2001 | Wulfman |

\* cited by examiner

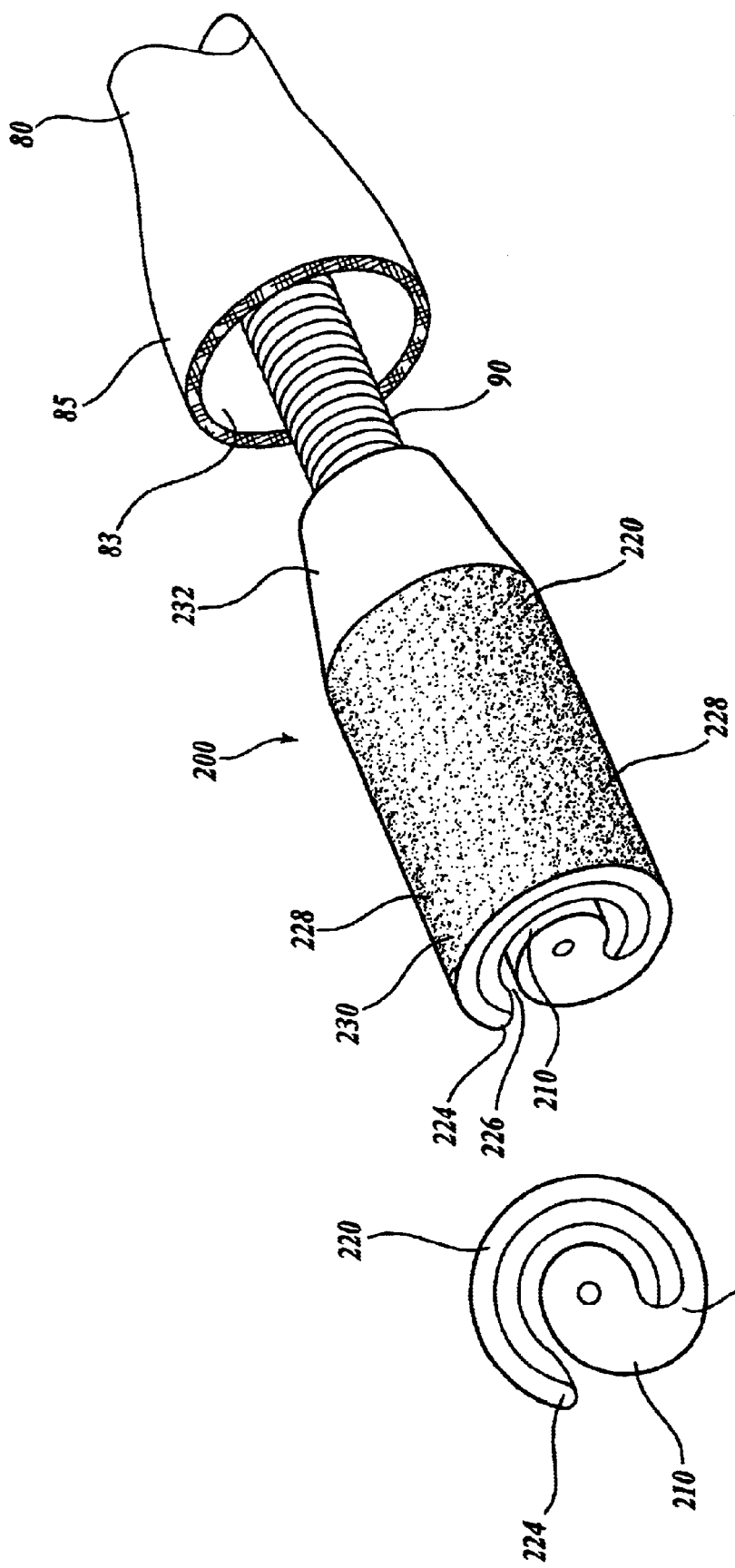

COMPRESSIBLE ATHERECTOMY BURR

FIELD OF THE INVENTION

The present invention relates to medical devices in general and, in particular, to atherectomy devices for removing occluding material from a patient's vessels.

BACKGROUND OF THE INVENTION

A number of vascular diseases, such as arteriosclerosis, are characterized by the buildup of deposits (atheromas) in the intimal layer of a patient's blood vessels. If the atheromas become hardened into calcified atherosclerotic plaque, removal of the deposits can be particularly difficult. Deposits in the vasculature can restrict the flow of blood to vital organs, such as the heart or brain, and can cause angina, hypertension, myocardial infarction, strokes, and the like.

To treat such diseases, many invasive and noninvasive techniques have been developed. For example, cardiac bypass surgery is now a commonly performed procedure whereby an occluded cardiac artery is bypassed with a segment of a healthy blood vessel that is obtained from elsewhere in the body. While this procedure is generally successful, it is traumatic to the patient because the entire chest cavity must be opened to access the site of the occluded vessel. Therefore, the procedure is not often performed on elderly or relatively frail patients.

As an alternative to cardiac bypass surgery, numerous atherectomy devices have been developed for removing such deposits in a less invasive manner. One such device that is particularly suited to removing calcified atherosclerotic plaque is an ablative rotational atherectomy device, such as that disclosed in U.S. Pat. No. 4,990,134 by Auth. Auth teaches using a small burr covered, or partially covered, with an abrasive cutting material, such as diamond grit, to remove the occluding deposit by ablation. A rotational atherectomy device practicing the Auth invention is sold by the assignee of the present invention under the trademark Rotablator™.

To perform the atherectomy procedure, a guide catheter is inserted into the patient, frequently at the femoral artery, and advanced through the patient's vasculature until the distal end of the guide catheter is located near a target occlusion. A guide wire is then inserted through the guide catheter and advanced past the occlusion. An atherectomy device having a flexible drive shaft attached to a small abrasive burr is then advanced through the guide catheter and over the guide wire to the point of the occlusion. The burr is then rotated at high speed and advanced through the occlusion to remove the deposit. The ablative process produces particles that are sufficiently small such that they will not re-embolize in the distal vasculature. As the burr removes the occlusion, a larger lumen is thereby created in the vessel, thereby improving blood flow through the vessel.

It is well recognized that the risk of certain patient complications increases with the size of the guide catheter through which minimally invasive devices are routed. Larger guide catheters require larger access holes in the femoral artery, creating the potential for patient complications, such as the sealing of the puncture site after completion of the procedure. Therefore, physicians generally wish to utilize the smallest possible guide catheter during a procedure. However, the smaller size guide catheters can only accommodate correspondingly smaller sized ablation burrs. Therefore, if a large vessel is to be treated, a larger burr and larger guide catheter must be used to successfully remove all of the occlusion from the patient's vessel.

In addition, existing ablation burrs are rigid, having a fixed diameter, and may require undesirably large forces to traverse larger occlusions. Therefore, currently many procedures are performed using multiple passes through the occlusion with ablation burrs of increasing diameter. While these procedures have proven effective, the use of multiple devices for a single procedure adds both time and cost to the procedure. Expandable rotational ablation burrs have been developed, such as those disclosed in U.S. Pat. No. 6,096,054, which is assigned to the assignee of the present invention. It is sometimes desirable, however, that the ablation burr have a fixed, well-defined maximum operating diameter. Expandable ablation burrs may have a maximum operating diameter that is a function of the rotational speed of the burr, or otherwise not provide sufficient dimensional stability for specific applications.

Given these desired operating characteristics, there is a need for an atherectomy device having a burr with a predictable, well-defined maximum operating diameter that can treat large occlusions without requiring multiple burrs and that can be routed to the occlusion site using a relatively small diameter guide catheter.

SUMMARY OF THE INVENTION

The invention disclosed herein is an atherectomy device utilizing a compressible burr, whereby the compressible burr can be advanced to and withdrawn from the site of an occlusion using a guide catheter having a diameter that is smaller than the operational diameter of the burr. Because the compressible burr expands in situ to its operational maximum diameter, a single burr can be used to ablate moderately thick occlusions, eliminating the need to use multiple burrs with graduated diameters.

According to a first embodiment of the invention, the atherectomy device includes an ablation burr attached to a drive shaft with a support member, the burr having at least one foldable, annular abrasive disk attached to the support member, and an abrasive nose member disposed forwardly from the support member, such that the ablation burr can fit within a guide catheter in a folded configuration.

In one aspect of the first embodiment, the foldable, annular disk has a plurality of radial cuts that extend from the edge of the disk part way towards the center. The radial cuts divide the annular disk into a plurality of disk segments that facilitate folding of the disk.

According to a second embodiment of the invention, the compressible burr comprises an elongate support member attachable to the drive shaft and a radially extending panel attached to the support member that extends in a spiral fashion outwardly from the support member. The panel is elastically compressible such that the panel can be elastically urged toward the support member.

In one preferred aspect of the second embodiment the panel includes a decreasing-diameter proximal portion that provides a ramp whereby retraction of the burr into the catheter will urge the panel toward a compressed configuration.

According to a third embodiment of the invention, the compressible burr comprises a hub fixedly attachable to the drive shaft having a plurality of flexible struts attached thereto. A compressible body substantially fills the volume created by the interior of the struts. The struts have an abrasive outer surface. The struts can flex inwardly to elastically compress the compressible body.

In one preferred aspect of the third embodiment, the struts comprise a generally convex back portion that form an increasing diameter portion of the burr and a generally concave forward portion that form a decreasing diameter portion of the burr.

According to a fourth embodiment of the invention, the compressible burr comprises a plurality of plastically deformable wires that are attached to the drive shaft in spaced-apart fashion at a distal end, and a flexible sheath having an ellipsoidal volume that encloses the plurality of wires. A portion of the outer surface of the flexible sheath is coated with abrasive particles, such as diamond particles, to produce an ablative surface. The plurality of wires can be deformed inwardly to decrease the diameter of the burr, and are selected to expand on spin-up of the burr, thereby inflating the sheath to its predetermined ellipsoidal shape, or designed to expand to size when released from a guide catheter, into which it may be withdrawn.

According to a fifth embodiment of the present invention, the compressible burr comprises a nose portion having an ablative leading surface, wherein the nose portion is attached to the drive shaft, and a resilient shell extends proximally from the nose portion. The resilient shell includes a compressible center portion having an abrasive outer surface. In one preferred aspect of the fifth embodiment, the shell includes a back portion that slidably engages the drive shaft such that when the center portion is compressed the back portion can move proximally. In one version of the fifth embodiment, the shell includes a back portion that is attached to the drive shaft, and has an elongate member extending forwardly to the nose portion. The center portion is open in the back and coaxially surrounds the elongate member of the back portion.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 2A and 2B illustrate a compressible atherectomy burr according to a second embodiment of the present invention;

DETAILED DESCRIPTION OF THE PREFERRED EMBODIMENT

Figure 1C:
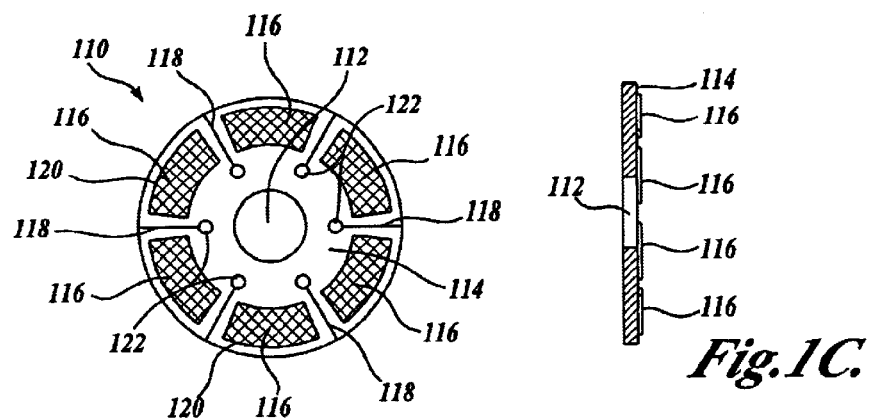
FIGS. 1A, 1B and 1C illustrate a compressible atherectomy burr according to a first embodiment of the present invention.

As explained in further detail below, the present invention is an atherectomy device having an ablation burr that can be compressed to a smaller diameter to facilitate insertion and removal of the ablation burr, but will expand to a fixed diameter during the atherectomy procedure. Referring now to the drawings, the compressible atherectomy burr of the present invention will be described.

Figure 1A:
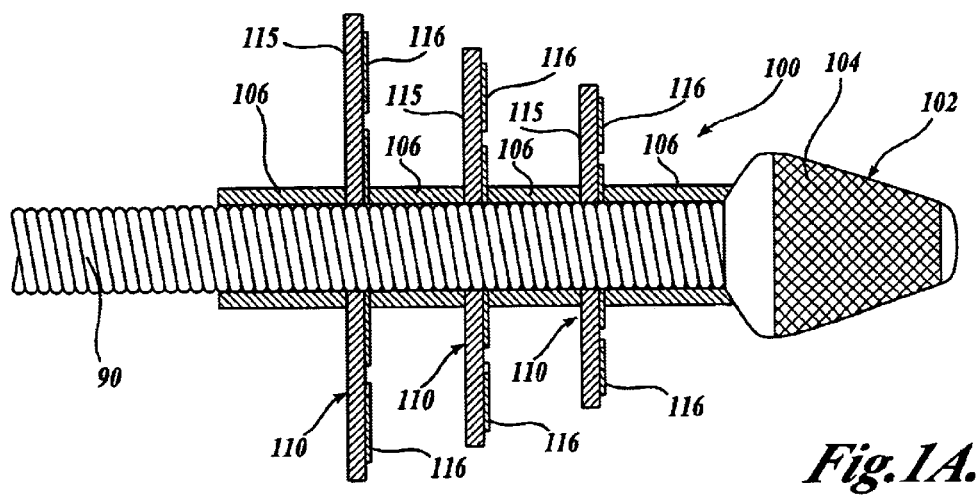
Figure 1B:
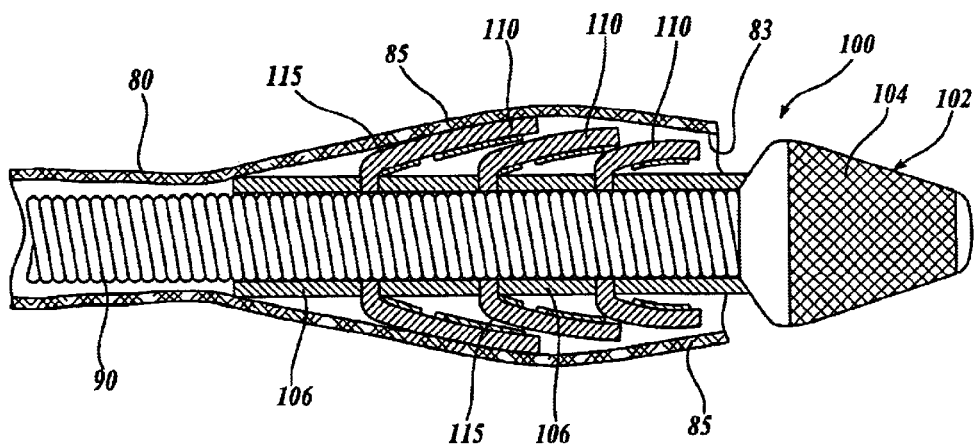

FIGS. 1A, 1B, and 1C illustrate a first embodiment of an atherectomy burr according to the present invention, wherein the burr 100 is attached to the end of a flexible drive shaft 90 that is disposed within a guide catheter 80. The burr 100 has a nose portion 102 with an abrasive leading surface 104. The abrasive leading surface 104 may be formed by affixing abrasive particles to the nose portion 102 or by making the nose portion 102 from a hard material, such as stainless steel, and machining or otherwise affecting an abrasive topography onto the surface of a hard material.

At least one annular flexible disk 110 is located behind or proximal to the nose portion 102. Three flexible disks 110 are shown in the preferred embodiment. The flexible disks 110 are made of polyurethane or other tough, flexible polymer, and have a center hole 112 that is approximately equal in diameter to the diameter of the drive shaft 90, and the flexible disks 110 slidably engage the drive shaft 90. A plurality of cylindrical spacers 106 are slidably inserted between the flexible disks 110, maintaining them in the desired spaced-apart relation. The flexible disks 110 are fixedly connected to the drive shaft 90 such that rotation of the drive shaft 90 will cause the flexible disks 110 to rotate correspondingly. The details of the connection between the flexible disks 110 and the drive shaft 90 are not critical to the present invention, and may be accomplished in a variety of ways. For example, the flexible disks 110 can be welded, brazed or glued to the drive shaft 90, or attached to the cylindrical spacers 106, which are then affixed to the drive shaft. Alternatively, the end portion of the drive shaft 90 could be provided with a keyed (noncircular) shape, and the center hole 112 made to match the keyed shape. Other methods of rotationally coupling the flexible disks 110 to the drive shaft 90 are well known in the art, and within the scope of the present invention.

The flexible disks 110 include a forward surface 114 having an abrasive portion 116 that preferably extends generally to the outer edge of the flexible disks 110. The abrasive portion 116 may be formed, for example, by affixing abrasive particles, such as diamond particles, to selected portions of the forward surface 114. Diamond particles may be attached to the forward surface 114 with an adhesive or a plating process, for example. In the preferred embodiment, the flexible disks 110 include a plurality of radial slots 118 that extend from the outer edge of the disks 110 part way to the center hole 112. The radial slots 118 divide the outer portion of the flexible disks 110 into a number of disk segments 120. The radial slots 118 may optionally terminate with a small hole 122, the small hole relieving the stress at the end of the slot 118 and decreasing the force required to bend the disk segments 120.

As seen most clearly in FIG. 1B, the flexible disks 110 are intended to deform, or fold over, to be slidably insertable into the guide catheter 80. The guide catheter 80 may include an expanded or fluted portion 85 at its distal end to accommodate the burr 100 with the folded flexible disks 110. The burr 100 can then be inserted to the location of the occlusion that is to be treated using a guide catheter 80 having a diameter that is smaller than the diameter of the unfolded burr 100. The catheter 80 can then be pulled back (or the drive shaft 90 pushed forward), releasing the burr 100 and permitting the flexible disks 110 to unfold to their full diameter. It will be appreciated that the flexible disks 110 have a well-defined maximum diameter that will not be significantly effected by spinning the drive shaft 90 at high rotation speeds. After the atherectomy procedure is completed, the drive shaft 90 can be pulled back into the distal end of the guide catheter 80 to fold the flexible disks 110 in order to remove the burr 100 from the patient's vasculature.

It may be desirable to coat the back surfaces 115 of the flexible disks 110 and/or an inner surface 83 of the guide catheter 80 with a hydrophilic coating, such as Hydropass™, available from Boston Scientific and described in U.S. Pat. No. 5,702,754. The hydrophilic coating attracts water molecules, thereby making the surfaces slippery, facilitating insertion and removal of the burr 100 into the catheter 80. In addition, the hydrophilic coating may be beneficial during ablation since less torque may be transferred to a vessel wall if the burr stalls. In addition, the differential cutting ability of the burr may be enhanced due to the increased ability of the burr to slide over soft tissues.

It will be appreciated that in addition to the advantages associated with insertion and removal of the burr 100, there may be further advantages of the flexible disks 100 during the atherectomy procedure. For example, the abrasive portions 116 are nominally oriented forwardly in the treated vessel, avoiding or minimizing undesirable contact between the abrasive portion 116 and the vessel wall. As the abrasive disks 110 encounter hardened occlusions in the vessel, forward motion of the flexible drive shaft 90 will cause the flexible disks 110 to bend backwardly, rotating the abrasive portions 116 toward the occlusion, thereby naturally enhancing the ablative action at the location of the hardened occlusion. Although this embodiment has been described and illustrated with three flexible disks 110, it will be appreciated that more or fewer flexible disks 110 may be used to accommodate the needs of a particular application, and would be within the scope of the present invention. It will also be appreciated that the flexible disk 110 could be made without the radial slots 118, thereby increasing the stiffness of the flexible disk 110, while still permitting it to deform into a folded condition for insertion and removal.

A second embodiment of a compressible burr according to the present invention is shown in FIGS. 2A and 2B. The burr 200 includes a centrally located cylindrical portion 210 that is fixedly and generally coaxially connected to a drive shaft 90 such that rotation of the drive shaft 90 will cause the burr 200 to rotate. The drive shaft 90 is covered over a substantial portion of its length with a guide catheter 80, which, in the preferred embodiment, includes a fluted portion 85. Although other attachment mechanisms are possible, in the preferred embodiment the central cylindrical portion 210 includes a center hole (not shown) through which the drive shaft 90 is inserted and fixedly attached using any suitable adhesive.

A thin panel of flap portion 220 extends radially outward from the central cylindrical portion 210 to form a generally circular cylindrical shell that partially surrounds the center cylindrical portion 210. The outer edge 224 of the panel portion 220 is disposed radially away from the center cylindrical portion 210 to form an elongate gap 226 between the outer edge 224 and the center cylindrical portion 210. The panel portion 220 is formed from a semi-rigid material, selected such that the panel portion 220 can be elastically compressed to close the gap 226, thereby decreasing the diameter of the burr 200.

The panel portion 220 includes a forward segment 230 that has a constant axial cross section, and a back segment 232 that tapers radially inward. The taper of the back segment 232 provides a ramp such that when the drive shaft 90 is retracted into the catheter 80, the tapered back segment 232 will slidably engage the lumen of catheter 80. As the drive shaft 90 is pulled further back into the catheter 80, the panel portion 220 will elastically compress thereby reducing the diameter of the burr 200 as it is pulled into the catheter 80, for easier insertion and extraction of the burr 200.

The forward segment 230 of the panel portion 220 includes one or more abrasive sections 228 on its exterior surface, providing an ablative surface for the atherectomy procedure. The abrasive portion 228 may be formed, for example, by affixing abrasive particles, such as diamond particles, to selected portions of the outer surface. It may be desirable to coat the back segment 232 of the panel portion 220 and/or the inner surface 83 of the fluted portion 85 of the guide catheter 80 with a hydrophilic coating to facilitate the retraction of the burr 200 into the catheter 80. As will be appreciated, the burr 200 is rotated such that the edge 224 trails the movement of the burr. In the embodiment shown in FIG. 2B, the burr 200 is always rotated clockwise. However, the burr could also be constructed to rotate counterclockwise as desired.

It is contemplated that this second embodiment of a burr 200 might also incorporate features of other atherectomy burrs described herein. For example, a smaller, forwardly facing nose portion, such as the nose portion 102 shown in FIG. 1A, could be added to the front of the burr 200 to produce a guide hole. Moreover, the panel portion 220 could include a tapered forwardmost segment (not shown) similar to the back segment 232, but facing forwardly, to facilitate engagement of the occlusion. In particular, a tapered forwardmost segment could taper to generally meet the widest portion of a nose portion, to produce a substantially continuous, increasing diameter, ablative surface. Alternatively, the burr could have a forward nose not contiguous with the flap.

Figure 3B:
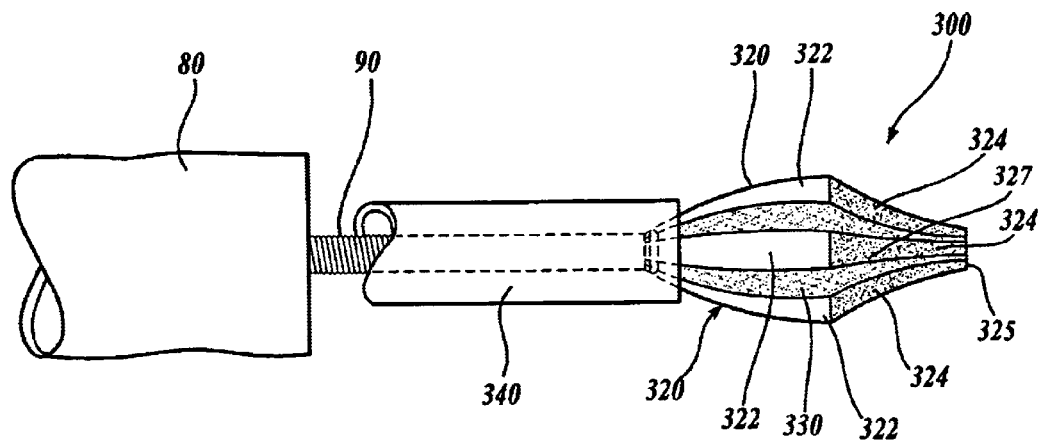
FIGS. 3A, 3B, and 3C illustrate a compressible atherectomy burr according to a third embodiment of the present invention.
Figure 3A:
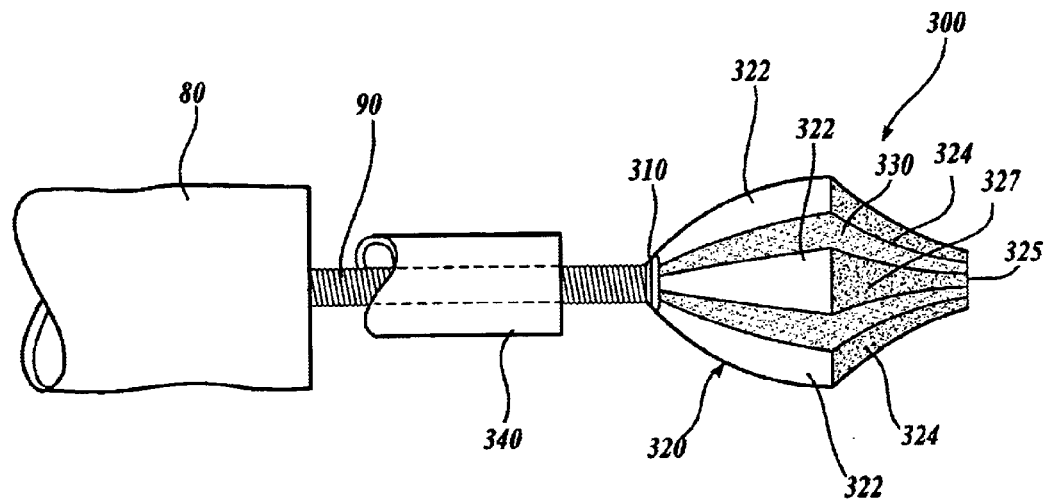

A third embodiment of a compressible burr according to the present invention is shown in FIGS. 3A and 3B. The burr 300 includes a rear hub 310 that is fixedly connected to a drive shaft 90 such that rotation of the drive shaft 90 will cause the burr 300 to rotate. The drive shaft 90 is covered over a substantial portion of its length with a guide catheter 80, that optionally includes a fluted portion at its distal end.

Figure 3C:
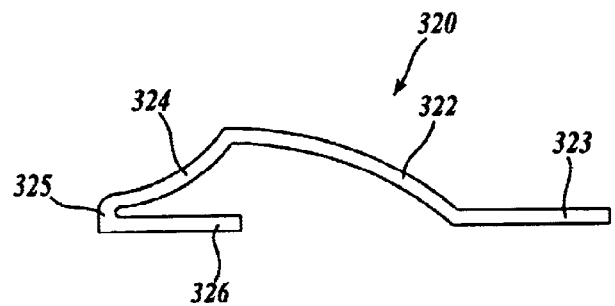

The burr 300 includes a plurality of flexible struts 320, each strut having a back portion 322 that is fixedly attached to the rear hub 310, a forward portion 324 that extends forwardly from the back portion 322, and a folded back portion 326, that extends backwardly from the distal end 325 of the forward portion 324. The plurality of flexible struts 320 are equally spaced around the perimeter of the hub 310, cooperatively defining a volume therebetween. As seen most clearly in FIG. 3C, which shows a side view of an individual strut 320, the back portion 322 is preferably longitudinally convex and includes a proximally extending tab portion 323 for attachment to the drive shaft 90. The forward portion 324 is preferably longitudinally concave. The outer surface of the forward portion 324 is coated with diamond particles 327 to provide an abrasive surface.

A compressible body 330, such as a hollow elastomeric bladder, is provided within the volume defined by the interior of the flexible struts 320. The flexible struts 320 are preferably attached to the compressible body 330, such that the compressible body 330 will generally maintain the flexible struts 320 in a spaced-apart configuration, while also permitting longitudinal flexure of the struts 320.

The burr 300 can be fabricated, for example, by stamping or wire electro-discharge machining, the flexible struts 320 from a suitable metal, then welding the flexible struts 320 at a proximal end 321 to the rear hub 310. A liquid injection molding process can then be used to create the compressible body 330 from silicone, or some other suitable material. Finally, any particulate abrasive, such as diamond particles can be attached to the forward portion 324 of the flexible struts 320.

It will be appreciated that the burr 300 can be deformed to a compressed state, as shown in FIG. 3B. The compressed state has a smaller maximum diameter than the relaxed, expanded state (shown in FIG. 3A). For example, a "pull-in" sheath 340 can be provided that slidably fits within the guide of catheter 80. When the drive shaft 90 is pulled backwardly, the burr 300 will be pulled against the pull-in sheath 340, such that the back portion 322 of the flexible struts 320 engage the sheath 340. Pulling the drive shaft 90 further will result in an inward force on the compressible body 330 from the back portions 322 of the struts 320, thereby permitting the sheath 340, and burr 300 to be retracted into the guide catheter 80. It will be appreciated that other means of compressing and retracting the burr 300 are also possible, including the use of a fluted catheter, as discussed above.

Figure 4A:
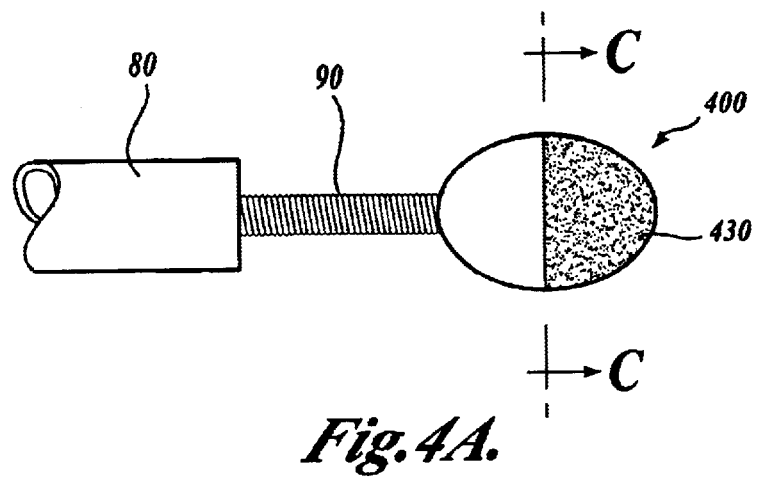
FIGS. 4A, 4B, 4C, and 4D illustrate a compressible atherectomy burr according to a fourth embodiment of the present invention.
Figure 4B:
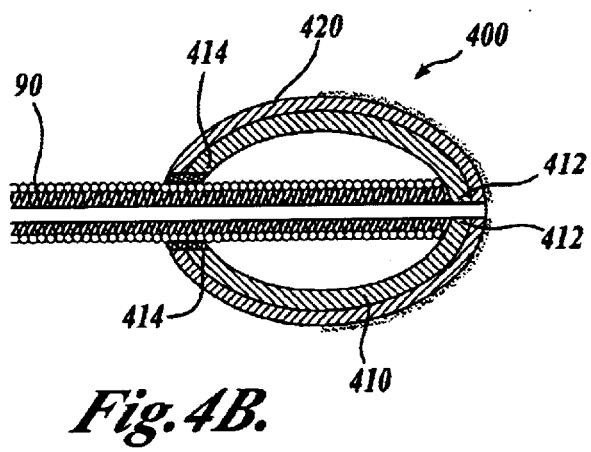
Figure 4C:
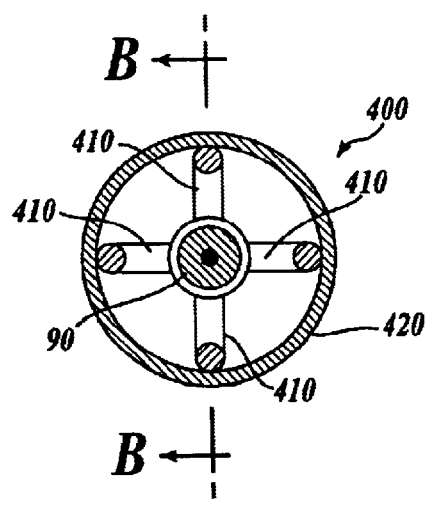

A fourth embodiment of a compressible burr according to the present invention is shown in FIGS. 4A, 4B, and 4C. The burr 400 is fixedly connected to a drive shaft 90 such that rotation of the drive shaft 90 will cause the burr 400 to rotate. FIG. 4A shows a side view of the burr 400 connected to a drive shaft 90, and FIG. 4B shows a cross-sectional view of the burr 400, taken along a axial center plane. The drive shaft 90 is covered over a substantial portion of its length with a guide catheter 80 that optionally includes a fluted portion at its distal end. The burr 400 includes a plurality of elongate flexible members or wires 410 (four shown in FIG. 4C), each wire 410 having a distal end 412 that is attached to the drive shaft 90, and a proximal end 414 extending proximally from the distal end 412 that is also attached to the drive shaft 90. The wires 410 are preferably equally spaced around the perimeter of the drive shaft 90, and may attach directly to the drive shaft 90 or attach through an intermediate hub (not shown) that connects to the drive shaft 90.

A resilient sheath 420, having a generally football shape or ellipsoidal shape, encloses the wires 410. The resilient sheath 420 is attached to the drive shaft 90, and may optionally also be attached to one or more of the wires 410. The sheath 420 is thin and sufficiently flexible to collapse, or fold in on itself, and strong enough to provide the working surface for the burr 400. An abrasive coating 430, such as a coating including diamond particles, is applied to the forward portion of the sheath 420 in the manner described below. The sheath 420 may be attached to the wires 410, for example, by use of an appropriate adhesive inside the sheath 420. The burr 400 may be spun while the adhesive is drying, to keep the adhesive at the outer surface for bonding the wires 410 to the sheath 420.

Figure 4D:
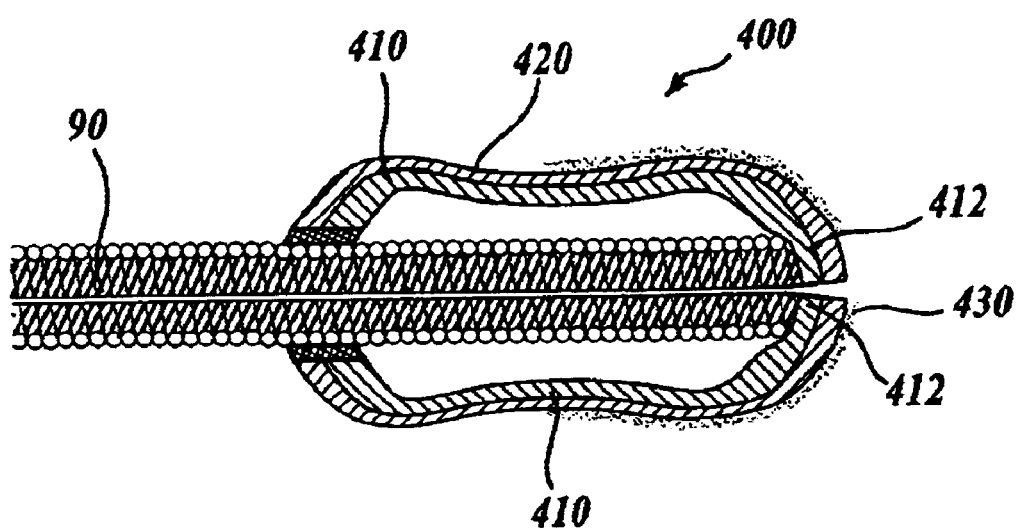

The plurality of wires 410 provide a support for the sheath 420, maintaining it in an uncompressed configuration, as shown in FIG. 4A, during the atherectomy procedure. To facilitate insertion and removal of the burr 400 through the vasculature of the patient, the burr 400 can be compressed by bending the wires 410 inwardly, as shown in FIG. 4D. The burr 400 can then be inserted through the guide catheter 80 to the site of the occlusion. The wires 410 are selected to have sufficient flexibility that upon spin-up of the burr for the ablation procedure, the wires 410 are forced outwardly by centrifugal forces, returning the burr 400 to the uncompressed configuration.

Alternatively, the wires 410 may be made from a resilient elastically deformable material formed to maintain the burr in the desired shape (which may or may not be ellipsoidal), the elastically deformable material being able to elastically compress sufficiently to allow the burr 400 to be inserted through the guide catheter 80, then elastically springing out to the desired shape when it is no longer constrained by the guide catheter 80. Another alternative is to use a so-called shape memory alloy, such as NiTi, for the wires 410. A shape memory alloy wire 410 is deformable to allow the burr to be compressed, but has a selectable preferred shape to which it will return (generally upon being heated).

Figure 5A:
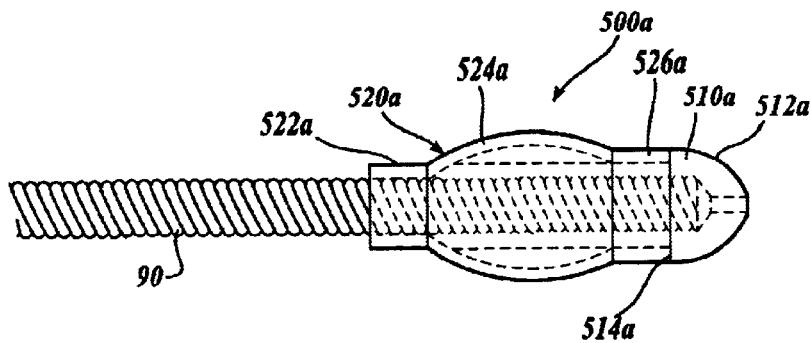
FIGS. 5A, 5B, 5C, and 5D illustrate two compressible atherectomy burrs according to a fifth embodiment of the present invention.
Figure 5B:
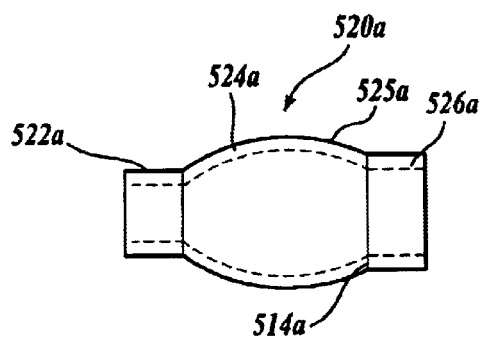
Figure 5C:
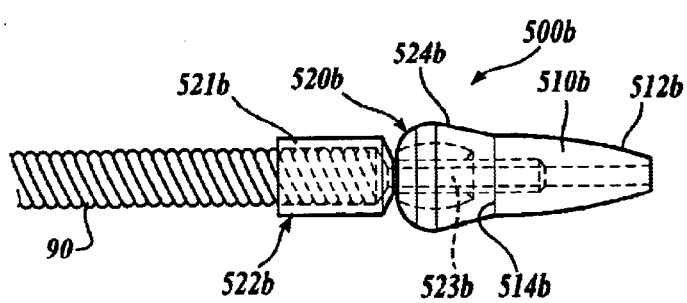

Two variations of a fifth embodiment of a compressible burr according to the present invention are shown in FIGS. 5A and 5C. The burr 500a, 500b is rotatably coupled to a drive shaft 90 such that rotation of the drive shaft 90 will cause the burr 500a, 500b to rotate. The burrs 500a, 500b include nose portions 510a, 510b having abrasive leading surfaces 512a, 512b that taper in the distal direction. The abrasive leading surface may be formed, for example, by affixing an abrasive material such as diamond particles to the leading surfaces 512a, 512b or by machining or otherwise roughing the leading surfaces 512a, 512b to create an abrasive topography. A resilient shell 520a, 520b is attached to back surfaces 514a, 514b of the nose, for example, by use of an adhesive. Each resilient shell 520a, 520b is shown most clearly in FIGS. 5B and 5C. A shell 520a, 520b is generally axisymmetric, and includes a collapsible center portion 524a, 524b that, in its uncollapsed state, has a greater outer diameter than the nose portion 510a, 510b.

The shells 520a, 520b may be made from any appropriate resilient material. In the preferred embodiment, a polyurethane polymer is used that having a low elasticity, so that the center portion 524a, 524b will not stretch when the burr is rotated at high speeds. The center portion 524a, 524b is provided with an abrasive outer surface 525a, 525b, at least over the forward part of the center portion 524a, 524b. The abrasive outer surface may be formed by affixing diamond particles, or other abrasive particles, to the center portion 524a, 524b as described below.

In the first variation of the burr 500a, shown in FIGS. 5A and 5B, the shell 520a includes a generally cylindrical proximal portion 522a extending backwardly from the center portion 524a, that is disposed coaxially around the drive shaft 90. The proximal portion 522a is preferably not affixed to the drive shaft 90, so that it can slide proximally or distally, to facilitate compression of the center portion 524a. A distal portion 526a of the shell 520a extends forwardly from the center portion 524a and is fixedly attached to the back surface 514a of the nose portion 510a. The nose portion 510a is attached to the drive shaft 90 such that rotation of the drive shaft will cause a corresponding rotation of the nose portion 510a. The distal portion 526a may optionally also have an abrasive outer surface. The resilient center portion 524a can be collapsed into the guide catheter (not shown) for easier insertion and removal of the burr 500a, and will expand to its uncompressed state as it is released from the guide catheter.

Figure 5D:
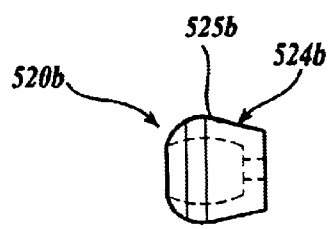

In the second variation of the burr 500b, shown in FIGS. 5C and 5D, the shell 520b is formed in two parts. A proximal portion 522b is made from a hard material such as stainless steel. The proximal portion 522b includes a generally cylindrical back section 521b that is fixedly connected to the drive shaft 90, and a smaller-diameter, elongate forward section 523b that extends coaxially forward. The nose portion 510b is attached to the distal end of the elongate forward section 523b. The nose portion may include an abrasive outer surface, similar to that described above. The resilient center portion 524b is attached to the back surface 514b of the nose portion 510b. The resilient center portion 524b has a maximum diameter that is greater than the diameter of the nose portion 510b that can be collapsed into the guide catheter (not shown) for easier insertion and removal of the burr 500b.

It will appreciated that collapsing these burrs 500a, 500b aids in insertion and removal of the burrs into the patient's vasculature by permitting the use of a guide catheter having a smaller diameter than the working diameter of the burrs 500a, 500b. Additionally, during the atherectomy procedure, as the burrs are rotated in the proximity of an occlusion, the resilient center portions 524a, 524b will flex to accommodate restricted passageways in the patient's vessels that are causes by the occlusion. The resilient center portions 524a, 524b and, in particular, the abrasive surfaces 525a, 525b will provide a gentle, outward pressure on the occlusion, facilitating the ablative removal of the occlusion during the procedure, and the burrs 500a, 500b will expand to the desired, predetermined maximum radius as the occlusion is removed.

In the various embodiments of the preferred embodiment described above, where abrasive particles are to be affixed to a polymeric burr element, any suitable method of affixing the particles may be used. For example, in the preferred embodiments, the abrasive is secured to the polymeric member by creating a thin base layer of silver using vacuum deposition techniques such as are well known in the art. Metalization of polymeric materials is discussed, for example, in U.S. Pat. No. 5,468,562 to Farivar, et al., and in the references cited therein. Once the silver base layer is applied to the polymeric member, a layer of metal such as nickel having a slurry of diamond particles disposed therein can be plated to the base layer using an electro- or electroless-plating method as is done with conventional burrs.

In some instances, it may be desirable to etch or mask a portion of the polymeric member with a patter of dots or other shapes so that the base layer does not completely surround the polymeric member. If the abrasive is only plated to the etched pattern, it may allow the polymeric member to more easily expand, collapse, or otherwise flex, and also enhance the adhesive stability of the abrasive coating. In the preferred embodiments, abrasive dots or pads having a diameter of approximately 0.010 to 0.015 inches are used.

In addition to electroplating, it is believed that other techniques could be used to secure the abrasive to the balloon, such as by using an adhesive or chemically bonding sites on the outer surface of the polymeric balloon to which metal ions such as copper, silver, gold, or nickel may bond. These sites may be bonded to the polymeric member using a high-vacuum plasma system or by incorporating chemicals (such as carbon, silver, etc.) with the polymer prior to fabrication of the polymeric member. Alternatively, it is believed that pulse cathode arc ion deposition could be used to incorporate bonding sites on the surface of the elastomer.

While the preferred embodiment of the invention has been illustrated and described, it will be appreciated that various changes can be made therein without departing from the scope of the invention. It is therefore intended that the scope of the invention be determined from the following claims and equivalents thereto.

What is claimed is:

1. An atherectomy device for ablating an occlusion in a patient's vessel, comprising:
    a flexible drive shaft;
    an ablation burr rotationally coupled to the drive shaft, the ablation burr having a proximal end including at least one flexible annular disk having a center hole and an outer edge, the annular disk having an abrasive disposed on a forwardly facing surface and a distal end comprising a nose member having an abrasive leading surface; and
    a catheter extending over the drive shaft, the catheter adapted to slidably receive the at least one flexible annular disk in a folded configuration, wherein portions of the flexible annular disk are rotated approximately 90° from an unfolded configuration;
    wherein the abrasive comprises a plurality of diamond particles affixed to the forwardly facing surface of the flexible annular disk.

2. The atherectomy device of claim 1, further comprising a support member secured to the drive shaft wherein the at least one flexible annular disk is received by the support member.

3. The atherectomy device of claim 2, wherein the at least one flexible annular disk has a plurality of radial cuts therethrough, the radial cuts each having a first end disposed at a location radially outward from the center hole and a second end disposed at the outer edge, the radial cuts defining a plurality of disk segments.

4. The atherectomy device of claim 3, wherein the at least one flexible annular disk further comprises a plurality of small holes disposed at the first end of each radial cut.

5. The atherectomy device of claim 3, wherein the at least one flexible annular disk comprises at least three flexible annular disks that are axially spaced apart and attached to the support member, the at least three flexible annular disks having different diameters.

6. The atherectomy device of claim 1, wherein diamond particles are affixed to the nose portion to form the abrasive leading surface.

7. The atherectomy device of claim 1 wherein the nose portion has an abrasive surface formed by machining grooves into the nose portion.

8. An atherectomy device for ablating an occlusion in a patient's vessel, comprising:
    a flexible drive shaft;
    an ablation burr rotationally coupled to the drive shaft, the ablation burr having a proximal end including at least one flexible annular disk having a center hole and an outer edge, the annular disk having an abrasive disposed on a forwardly facing surface and a distal end comprising a nose member having an abrasive leading surface, the annular disk being deformable between a planar orientation wherein the annular disk is substantially flat and a folded orientation wherein a portion of the annular disk is rotated about 90° from the planar orientation; and
    a catheter extending over the drive shaft, the catheter adapted to slidably receive the at least one flexible annular disk in the folded orientation.

9. The atherectomy device of claim 8, further comprising a support member secured to the drive shaft wherein the at least one flexible annular disk is received by the support member.

10. The atherectomy device of claim 9, wherein the at least one flexible annular disk has a plurality of radial cuts therethrough, the radial cuts each having a first end disposed at a location radially outward from the center hole and a second end disposed at the outer edge, the radial cuts defining a plurality of disk segments.

11. The atherectomy device of claim 10, wherein the at least one flexible annular disk further comprises a plurality of small holes disposed at the first end of each radial cut.

12. The atherectomy device of claim 10, wherein the at least one flexible annular disk comprises at least three flexible annular disks that are axially spaced apart and attached to the support member, the at least three flexible annular disks having different diameters.

* * * * *